United States Patent [19]
Schmidt et al.

[11] Patent Number: 5,277,711
[45] Date of Patent: Jan. 11, 1994

[54] MIXTURES USEFUL AS LUSTER PIGMENTS

[75] Inventors: Helmut Schmidt, Osthofen; Werner Ostertag, Gruenstadt; Norbert Mronga, Dossenheim; Raimund Schmid, Neustadt, all of Fed. Rep. of Germany

[73] Assignee: BASF Aktiengesellschaft, Ludwigshafen, Fed. Rep. of Germany

[21] Appl. No.: 28,285

[22] Filed: Mar. 9, 1993

[30] Foreign Application Priority Data

Mar. 21, 1992 [DE] Fed. Rep. of Germany ....... 4209242

[51] Int. Cl.⁵ .......... C09C 1/64; C04B 14/20; B05D 7/00; B05D 5/06
[52] U.S. Cl. .................. 106/404; 106/418; 427/213; 427/258
[58] Field of Search ........... 106/404, 418; 427/213, 427/258

[56] References Cited

U.S. PATENT DOCUMENTS

| | | | |
|---|---|---|---|
| 3,087,829 | 4/1963 | Linton | 106/418 |
| 3,708,318 | 1/1973 | Reinhart et al. | 106/404 |
| 3,926,659 | 12/1975 | Bernhard et al. | 106/417 |
| 4,146,403 | 3/1979 | Armanini et al. | 106/404 |
| 4,323,554 | 4/1982 | Bernhard | 106/404 |
| 4,328,042 | 5/1982 | Ostertag et al. | 106/404 |
| 4,344,987 | 8/1982 | Ostertag et al. | 106/418 |
| 4,978,394 | 12/1990 | Ostertag et al. | 106/404 |
| 5,112,403 | 5/1992 | Okura et al. | 106/418 |

OTHER PUBLICATIONS

4029 World Surface Coatings Abstracts, vol. 53, No. 460, Oct. 1980 Old Woking, Surrey Gr. Britain, p. 1261.
Derwent Abstract J54081337, Showa Aluminum KK, 1977.

Primary Examiner—Helene Klemanski
Attorney, Agent, or Firm—Oblon, Spivak, McClelland, Maier & Neustadt

[57] ABSTRACT

Mixtures useful as luster pigments for coloring paints, printing inks, plastics, decorative cosmetic preparations and ceramic products and usable in dry form in printing and coating processes consist of
A) iron oxide-coated aluminum particles and
B) iron oxide-coated mica particles with or without a prior coating of a colorless, highly refractive metal oxide as essential components.

4 Claims, No Drawings

MIXTURES USEFUL AS LUSTER PIGMENTS

The present invention relates to novel mixtures useful as luster pigments, comprising
A) iron oxide-coated aluminum particles and
B) iron oxide-coated mica particles with or without a prior coating of a colorless, highly refractive metal oxide
as essential components.

The invention further relates to the preparation of these mixtures and to the use thereof as dry pigments in printing and coating processes and generally for coloring paints, printing inks, plastics, decorative cosmetic preparations and ceramic products.

Luster or effect pigments are increasingly used in many sectors of industry, for example in automotive coatings, decorative coatings, plastics pigmentation, printing inks, in particular encaustic inks, paints, and in cosmetics.

Their optical effect is based on directional reflection at predominantly sheetlike, oriented metallic or strongly refractive pigment particles. According to the nature of the pigment particles, the pigments are also referred to as metal effect pigments (eg. aluminum, zinc, copper or alloys thereof) or pearl luster pigments (eg. based on coated mica such as muscovite, phlogopite and biotite, talc or glass).

Luster pigments may have a multiphase structure, formed by coating the starting substrates with thin films of highly refractive oxides such as chromium(III) oxide, in particular iron oxide and titanium oxide. Interference with or without absorption will in these cases result in a multiplicity of colors depending on the thickness of the oxide layer; therefore these pigments are also called interference pigments.

As a result of the incident light being reflected directionally at the platelet like pigment particles, coated luster pigments that are oriented, for example in perceived color (lightness and/or hue and/or chroma) varies with the angle of illumination or observation. These effects can be ascribed to a complex interplay of reflection and transmission of the incident light, the color of which can be affected by phenomena due to the pigment particles, such as interference in thin films and absorption by colored centers.

Examples of such pigments are the iron oxide-coated aluminum and mica pigments described respectively in EP-A-33457 on the one hand and EP-A-45851 and U.S. Pat. No. 3,087,829 on the other.

The $Fe_2O_3$-coated aluminum pigments described in EP-A-33457 are especially of interest for obtaining yellows, golds and reds of high brilliance and also, in contradistinction to mica pigments, high hiding power.

However, disadvantages of these pigments are that their powders are readily ignitable in air and represent a dust explosion hazard, so that they need to be employed in the form of pigment pastes, moistened for example with heavy ligroine, and cannot be employed in the form of dry pigments. This is true in particular of printing and coating processes, for example in bronze printing, whereby the press applies an unpigmented binder solution and the bronzer then dusts dry pigment onto the wetted areas. Another problem is industrial production of $Fe_2O_3$-coated aluminum pigments at high iron oxide contents.

It is an object of the present invention to reduce or eliminate the ignitability of and the dust explosion hazard represented by aluminum pigments coated with iron oxide, in particular with $Fe_2O_3$.

We have found that this object is achieved by mixtures comprising A) iron oxide-coated aluminum particles and B) iron oxide-coated mica particles with or without a prior coating of a colorless, highly refractive metal oxide as essential components.

We have also found a process for preparing these mixtures, which comprises coating the aluminum and mica mixtures, which comprises coating the aluminum and mica particles conjointly with iron oxide in a fluidized bed by gas phase decomposition of iron carbonyls in the presence of oxygen and, if desired, water vapor.

We have also found a use for these mixtures as dry pigments in printing and coating processes and a process for producing printed or coated articles, which comprises first applying a binder layer to the as yet unprinted or uncoated articles in a conventional manner and subsequently applying the mixtures in the form of dry pigments by dusting or spraying.

Finally we have also found a general use for the mixtures in the coloring of paints, printing inks, plastics, decorative cosmetic preparations and ceramic products.

The mixtures of the invention contain in general from 5 to 50% by weight of component A and from 50 to 95% by weight of component B, preferably from 15 to 40% by weight of A and from 60 to 85% by weight of B, particularly preferably from 25 to 35% by weight of A and from 65 to 75% by weight of B. The mixtures may of course additionally contain additives customary for the particular intended use.

Surprisingly, the presence of the pearl luster pigment distinctly reduces the fire and dust explosion hazards posed by the $Fe_2O_3$-coated aluminum pigment. The pigment mixtures do not represent dust explosion hazards and are very difficult to ignite. For instance, contact with 500° C. bodies in air does not ignite the mixtures of the invention, while the ignition temperature of the pure $Fe_2O_3$-coated aluminum pigment is 360° C. Moreover, following local action of a sufficiently strong source of ignition, there is no flame propagation, while powders of $Fe_2O_3$-coated aluminum particles are observed to burn completely under similar conditions.

Preference is given in particular to $Fe_2O_3$-coated aluminum pigments, since they produce in particular brilliant and highly lustrous yellows, golds and reds.

The platelet like aluminum substrate particles can be produced by blanking from aluminum foil or by known atomization or grinding processes, and generally have an average particle diameter of from 10 to 120 $\mu$m. The particle size is advantageously adapted to the particular use. For bronze printing, for example, average particle diameters of from 10 to 50 $\mu$m are preferred, while for use in lacquers the average particle diameter should preferably be from 12 to 24 $\mu$m.

The coated aluminum pigments generally contain from 5 to 65, preferably from 10 to 55, % by weight of $Fe_2O_3$.

The colors obtained depend in the well-known way not only on the size of the particles but also in particular on the thickness of the oxide layer. For instance, as the thickness increases the color passes in succession through pale yellow, yellow, gold, red, violet, grayish yellow, grayish gold, reddish gold, cherry red.

For example, the dry pigment powder with a specific surface area (BET) of 2.5 $m^2/g$ has a golden color when the $Fe_2O_3$ content is from 16 to 22% by weight ($Fe_2O_3$ layer thickness about 25 nm) and a cherry red color when the $Fe_2O_3$ content is from 45 to 60% by weight (layer thickness about 115 nm).

The iron oxide-coated mica pigments used in the mixtures of the invention and the preparation of said pigments are known from EP-A-45851.

Again, especially the $Fe_2O_3$-coated mica flakes are preferred, which in general contain from 5 to 65, preferably from 10 to 55, % by weight of $Fe_2O_3$.

Suitable mica is in particular light-colored or white, and flakes of preferably wet-ground muscovite are particularly preferred. It is of course also possible to use other foliar silicate flakes such as phlogopite, artificial mica or glass flakes. Moreover, the mica particles may already bear a layer of a colorless highly refractive metal oxide, in particular titanium dioxide or zirconium dioxide. Pigments of this type are known for example from U.S. Pat. No. 3,087,828.

The mica particles have in general average particle sizes in the main dimension of from 5 to 400 μm, preferably from 10 to 100 μm, in particular from 30 to 70 μm, while their average thickness is in general from 0.03 to 30 μm, preferably from 0.2 to 5 μm.

As with the coated aluminum pigments, the color of the coated mica pigments depends not only on the particle size but also on the $Fe_2O_3$ content. For instance, the dry mica pigments that have an average particle size of from 5 to 50 μm and a specific surface area (BET) of about 3 $m^2/g$ are yellow or golden if the $Fe_2O_3$ content is from 10 to 25% by weight ($Fe_2O_3$ layer thickness about 25 nm) and red if the $Fe_2O_3$ content is from 45 to 55% by weight (layer thickness about 120 nm).

In the novel process for producing the novel pigment mixtures, aluminum and mica particles are conjointly coated with iron oxide in a fluidized bed by gas phase decomposition of iron pentacarbonyl.

The process is conveniently carried out as follows. A mixture of the pigment particles in the desired weight ratio is initially fluidized in a heatable fluidized bed reactor, for example as described in EP-A-33 457, using a fluidizing gas which is introduced through a plurality of nozzles attached at the side in the lower part of the reactor and which should not contain more than 5% by volume of oxygen, ie. preferably using an appropriate nitrogen-air mixture, and then heated, generally to 100°–400° C., preferably 180°–250° C.

Electrostatic charge buildups can advantageously be avoided by passing water vapor into the reactor at the same time. This can be done simply by passing all or some of the fluidizing gas through hot water, where it will pick up water vapor, or by introducing the water vapor through an additional nozzle at the side.

When the reaction temperature has been reached, vaporized iron carbonyl, in particular iron pentacarbonyl, preferably a mixture thereof with an inert gas such as nitrogen or argon, is introduced through a nozzle and oxidized in the reactor under controlled conditions. To obtain uniform coating of the pigment particles with iron oxide, the concentration of the iron pentacarbonyl vapor, based on the total amount of gas introduced into the reactor, should in general be not more than 5% by volume, preferably not more than 1% by volume.

By varying the duration of the treatment, the concentration of the gaseous carbonyl and the ratio of added iron pentacarbonyl to initially charged pigment particles it is possible to produce in a controlled and reproducible manner pigments ranging in color from light golden yellow to dark violet.

Once the desired color has been achieved, which can be discerned from a sample, the reactor is cooled down, and the cooled-down product is discharged.

It is a particular advantage that the manufacturing process of the invention permits trouble-free production of aluminum pigments having an $Fe_2O_3$ content of greater than 20% by weight, in particular interesting red pigments having an $Fe_2O_3$ content of about 45–60% by weight, even on an industrial scale, since excessive reaction of the reactor contents in the manner of a Thermit ® reaction ($2Al + Fe_2O_3 \rightarrow Al_2O_3 + 2Fe$) is prevented by the presence of the mica particles.

Of course, the mixtures according to the invention, in particular those having relatively low $Fe_2O_3$ contents, may also be obtained by subsequent mixing of the previously coated components in a liquid medium such as ethanol or acetone and subsequent drying, or dry under a protective gas such as nitrogen or argon, preferably directly in a fluidized bed following coating of the aluminum particle. In this case it is possible to achieve additional interesting coloristic effects by mixing differently colored components, for example a golden aluminum pigment with a yellow to reddish violet mica pigment.

The mixtures of the invention can in principle be used in any sector of industry customary for luster pigments. It is particularly advantageous that they are safe to handle even in the dry state and hence can be used for example in printing and coating processes in which a dry pigment is employed.

An example of such a process is bronze printing, whereby, as mentioned earlier, the press initially applies only a binder solution and the wetted areas are subsequently dusted with dry pigment. The exact procedure to be employed for the purposes of the invention is that employed in general. Suitable binders are the customary ones such as linseed oil varnish and phenol-modified rosin esters.

The mixtures of the invention are notable for their particularly advantageous coloristics, their binding power, their high yield and their economy of use. They are neither a fire nor a dust explosion hazard even in the dry state. They can be used to produce in particular brilliant red to yellow and gold shades. Especially the red pigments applied in a lacquer show off not only their intensive red but also the metallic luster of the aluminum substrate, making them particularly interesting luster pigments.

EXAMPLES

A. Preparation of Mixtures According to the Invention

A.1 Preparation by conjoint coating of aluminum and mica particles.

EXAMPLE 1

A mixture of 60 g of aluminum, made up of 30 g of an aluminum powder with an average particle diameter of 20 μm and a BET surface area of 4.5 $m^2/g$ and 30 g of a coarser aluminum powder (average particle diameter 60 μm, BET surface area 1.5 $m^2/g$), and 140 g of ground mica (average particle diameter <100 μm) was heated to 180° C. in an externally heatable fluidized bed reactor made of glass, having a diameter of 8 cm and a height of 80 cm, and equipped with a glass frit bottom and filter socks, suspended from the top and to be cleaned with a nitrogen jet, and a gas injection nozzle situated on the side above the frit bottom. The total fluidizing gas rate was 1,000 l/h, made up of straight nitrogen at 400 l/h, nitrogen passed through a room temperature reservoir of iron pentacarbonyl at 400 l/h, and air passed through 40° C. water at 200 l/h. Over 20 h a total of 840 g of iron pentacarbonyl was introduced into the reactor a little at a time and deposited as an iron oxide film onto the plateletlike substrates. After cooling, the product was discharged.

The red pigment obtained had an $Fe_2O_3$ content of 51.5% by weight and exhibited high luster, high color strength and high hiding power. It was not ignitable by spark or flame.

EXAMPLE 2

Example 1 was repeated using a mixture of 60 g of aluminum (average particle diameter 60 μm, BET surface area 1.5 m²/g) and 140 g of the mica pigment Flonac ® ME 11 (Kemira Oy, Pori, Finland) and introducing a total of 145.3 g of iron pentacarbonyl a little at a time over 10 h.

The golden pigment obtained had an $Fe_2O_3$ content of 12.0 g by weight and exhibited high luster.

EXAMPLE 3

Example 1 was repeated in a somewhat larger fluidized bed reactor using a mixture of 260 g of aluminum (average particle diameter 20 μm, BET surface area 4.5 m²/g) and 600 g of ground mica (average particle diameter <100 μm), fluidizing for the total fluidizing gas rate of 2,300 l/h (straight nitrogen 1,500 l/h, iron pentacarbonyl-loaded nitrogen 400 l/h and moist air at 400 l/h) and introducing 1,670 g of iron pentacarbonyl over 30 h a little at a time.

The golden pigment obtained had an $Fe_2O_3$ content of 44.3% by weight and exhibited high luster.

EXAMPLE 4

Example 3 was repeated using 1,960 g of iron pentacarbonyl, added a little at a time over 40 h.

The reddish orange pigment obtained had an $Fe_2O_3$ content of 48.6% by weight and exhibited high luster.

A.2 Preparation by mixing previously coated aluminum and mica particles.

EXAMPLE 5

A mixture of 1 kg of a golden, iron oxide-coated aluminum pigment (78% by weight of Al, 22% by weight of $Fe_2O_3$, particle diameter 10-48 μm) and 2 kg of a golden, iron oxide-coated mica pigment (77% by weight of muscovite, 23% by weight of $Fe_2O_3$, particle diameter 10-48 μm) was stirred under nitrogen in 10 l of acetone in a stirred kettle for 10 min, filtered off and dried at 105° C.

EXAMPLE 6

Example 1 was repeated without mica to prepare 40 g of a golden, iron oxide-coated aluminum pigment (80% by weight of Al, 12% by weight of $Fe_2O_3$, particle diameter 10-65 μm). After cooling, 60 g of a golden, iron oxide-coated mica pigment (75% by weight of muscovite, 2% by weight of $TiO_2$, 23% by weight of $Fe_2O_3$, particle diameter 10-65 μm) were introduced. This mixture was fluidized with 350 l of nitrogen for 15 min and discharged.

COMPARATIVE EXAMPLE CE

Example 1 was repeated without mica to coat aluminum platelets with $Fe_2O_3$. The resulting golden pigment contained 22% by weight of $Fe_2O_3$.

B. Determination of Ignitability, Ignition Temperature and Dust Explosion Hazard The ignitability of the pigment powders in air was determined in accordance with 84/449/EEC Schedule A 10. The ignition sources used were a 2 cm methane gas flame, cerium-iron sparks and a gunpowder ignition jet. The quantity measured is the shortest burn-off time of a trail of the pigment powder 100 mm in length. Substances whose shortest burn-off times are below 45 sec are deemed easily ignitable.

To determine the ignition temperature the pigment powders were each contacted in air with a hot plate at from 100° to 800° C. The ignition temperature is the lowest temperature of a hot surface at which a sample-air mixture of optimum composition will just ignite under defined conditions.

The dust explosion hazard posed by the pigment powders was measured in an open Hartmann tube, an upright 1.2 l capacity glass tube sealed at the bottom and loosely closed at the top by a hinged lid. Dust samples were whirled up with air in the tube in concentrations of from 30 to 1,000 g/m³ and subjected to ignition tests using permanent electric sparks (energy about 4 Joule) and a glowing wire coil (about 1,200° C.) as ignition sources.

The results of the tests are summarized in the following table:

TABLE

| Ex. | Ignitability | Ignition temperature [°C.] | Dust explosion hazard |
| --- | --- | --- | --- |
| 5 | low | >500 | none |
| 6 | low | >500 | none |
| CE | easy | 360 | marked |

The pigment mixtures of Examples 1 to 3 compared with the unmixed $Fe_2O_3$-coated aluminum pigment do not represent a dust explosion hazard and, what is more, are slow to ignite.

C. Use of Mixtures According to the Invention

EXAMPLE 1C

In a sheet-fed offset press with an attached bronze printing duct, paper sheets for wine labels (brand name Chromolux ®, from Teraset) were initially offset printed with an unpigmented adhesive bronzing varnish composed of 95% by weight of linseed oil varnish and phenol-modified rosin ester and 5% by weight of polyvinyltoluene and then immediately transported into the bronzing station, where they were dusted with the pigment mixture of Example 5. Excess pigment powder was removed by a velvet doctor.

The printing speed was 2,600 sheets/h. The consumption was only 0.9 kg of pigment, while 2.7 kg of a conventional metal pigment (gold copper/zinc pigment) were consumed under similar conditions.

The printed wine labels showed a high-luster gold colored imprint of high hiding power. Soiling of the unprinted areas of the paper by adhering excess pigment powder was not observed.

EXAMPLE 2C

Example 1C was repeated using the pigment mixture of Example 6.

The printing speed was 2,500 sheets/h, and the pigment consumption was 1.9 kg for the same motive as in Example 1C.

The printed wine labels showed a high-luster bleached gold imprint of high hiding power.

EXAMPLE 3C

Example 1C was repeated using the pigment mixture of Example 2.

The printing speed was 2,300 sheets/h and the consumption was 2.0 kg of pigment.

The printed labels showed a high-luster red imprint exhibiting a pronounced angle dependence of the hue and of the reflected lightness.

We claim:

1. Mixtures useful as luster pigments, comprising
   A) iron oxide-coated aluminum particles and
   B) iron oxide-coated mica particles with or without a prior coating of a colorless, highly refractive metal oxide as essential components.

2. Mixtures as claimed in claim 1 consisting essentially of
   A) from 5 to 50% by weight of the aluminum particles and
   B) from 50 to 95% by weight of the mica particles.

3. A process for preparing the mixtures of claim 1, which comprises coating the aluminum and mica particles conjointly with iron oxide in a fluidized bed by gas phase decomposition of iron carbonyls in the presence of oxygen and, optionally, water vapor.

4. A process for producing printed or coated articles, which comprises first applying a binder layer to the as yet unprinted or uncoated articles in a conventional manner and subsequently applying the mixtures of claim 1 in the form of dry pigments by dusting or spraying.

* * * * *